United States Patent
Ludwig et al.

(10) Patent No.: US 8,031,834 B2
(45) Date of Patent: Oct. 4, 2011

(54) TOMOSYNTHESIS APPARATUS AND METHOD TO OPERATE A TOMOSYNTHESIS APPARATUS

(75) Inventors: Jasmina Ludwig, Munich (DE); Thomas Mertelmeier, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 40 days.

(21) Appl. No.: 12/573,986

(22) Filed: Oct. 6, 2009

(65) Prior Publication Data

US 2010/0091940 A1     Apr. 15, 2010

(30) Foreign Application Priority Data

Oct. 6, 2008 (DE) .......................... 10 2008 050 571

(51) Int. Cl.
*G01N 23/00* (2006.01)
(52) U.S. Cl. .......................................... 378/22; 378/37
(58) Field of Classification Search .............. 378/21–27, 378/37, 145, 147–148, 150, 151
See application file for complete search history.

(56) References Cited

U.S. PATENT DOCUMENTS

| 2004/0066904 A1 | 4/2004 | Eberhard et al. |
| 2007/0217569 A1* | 9/2007 | Barth et al. ..................... 378/22 |
| 2008/0164419 A1* | 7/2008 | Johnston et al. ......... 250/370.09 |

FOREIGN PATENT DOCUMENTS

DE       10 2006 024 413 A1       11/2007

* cited by examiner

*Primary Examiner* — Hoon Song
(74) *Attorney, Agent, or Firm* — Schiff Hardin LLP

(57) ABSTRACT

A tomosynthesis apparatus has an x-ray source that generates an x-ray beam emanating from a focus, which is received by a flat panel detector. To set a tomosynthesis angle, the position of the central axis of the x-ray beam of the x-ray source is variable. A collimator diaphragm has a diaphragm aperture that limits the expansion of the x-ray beam at the location of the flat panel detector. The collimator diaphragm is arranged in the beam path between the focus and the flat panel detector. The shape and size of the diaphragm aperture are dynamically varied (adjusted) dependent on the changing tomosynthesis angle, such that the expansion of the x-ray beam at the location of the flat panel detector always essentially corresponds to the detector dimensions.

16 Claims, 5 Drawing Sheets

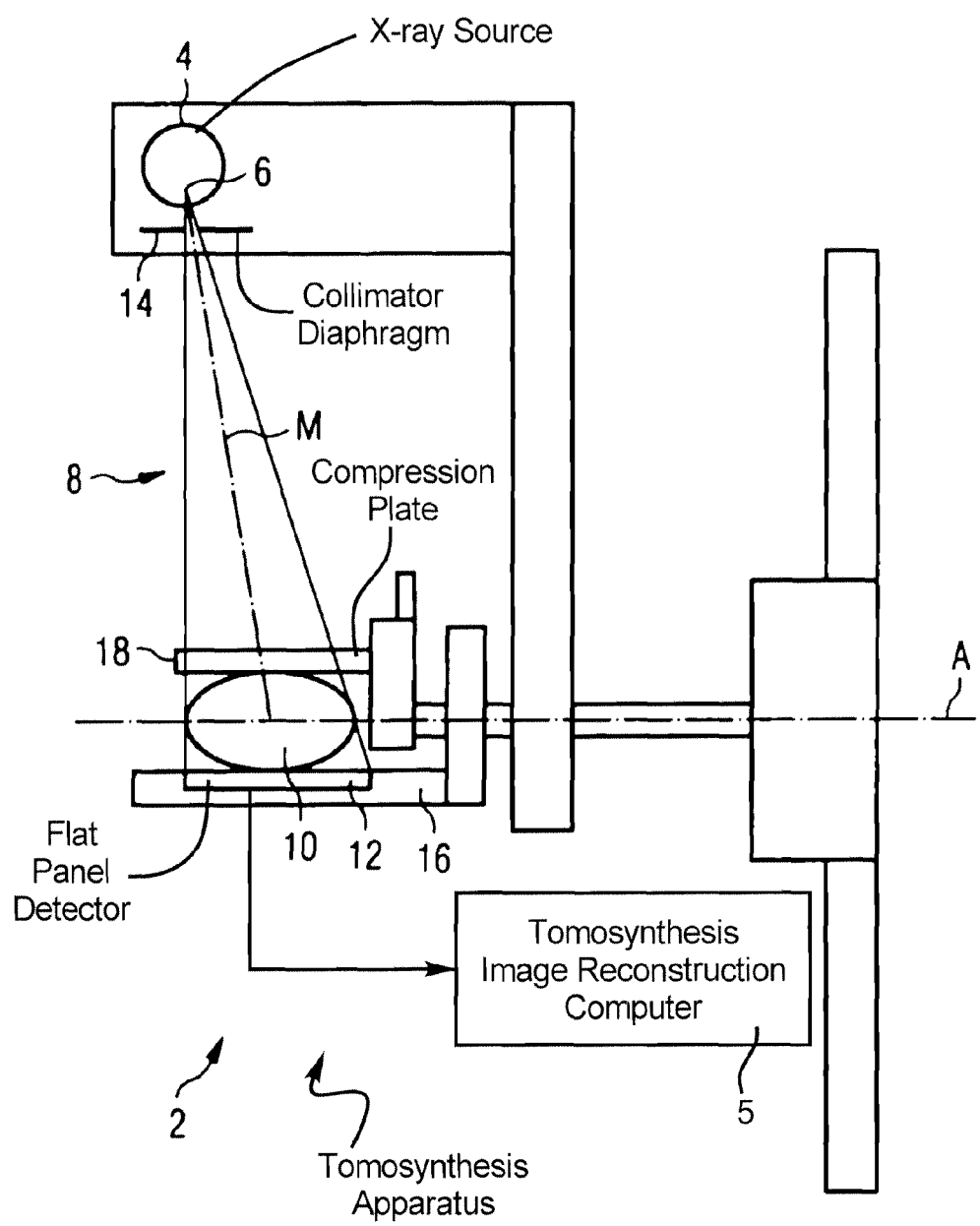

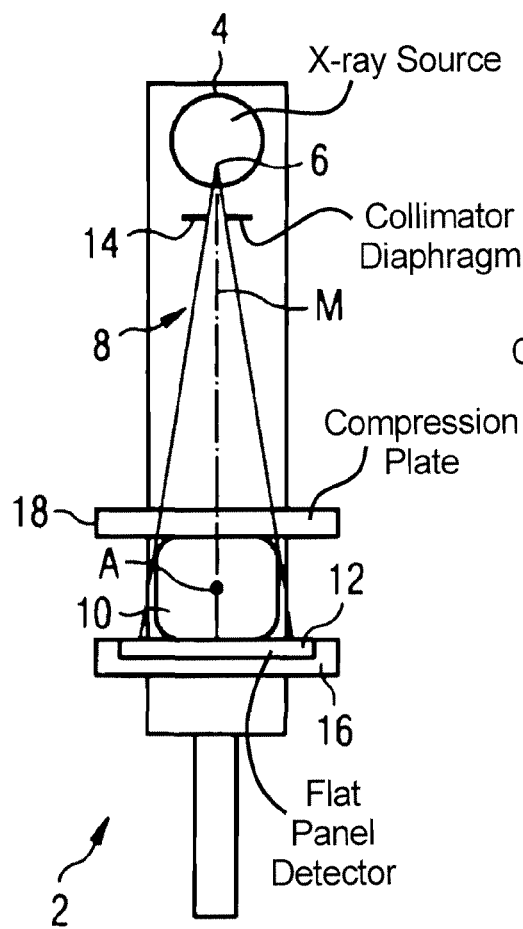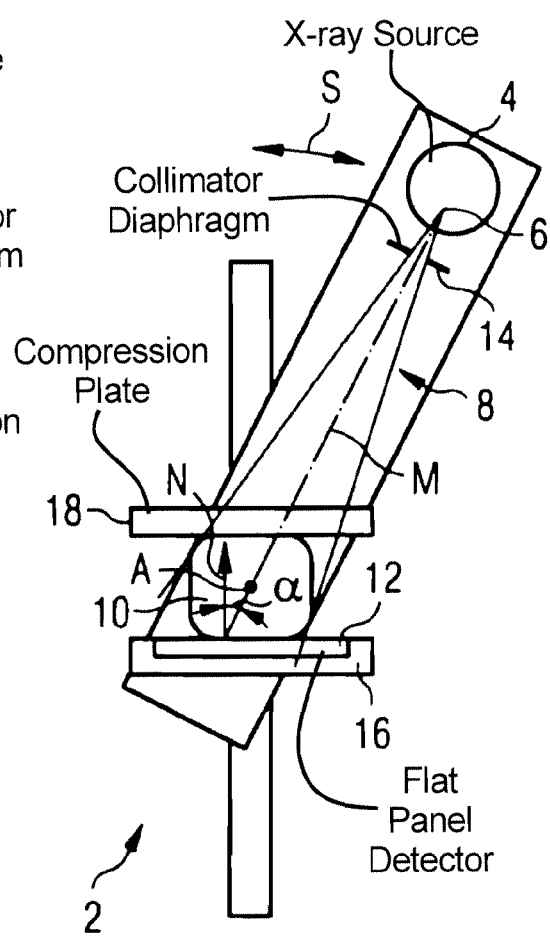

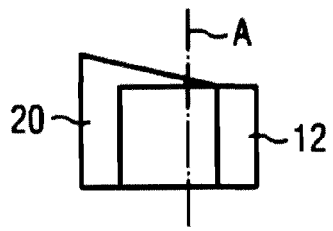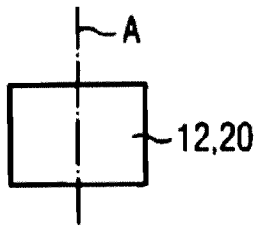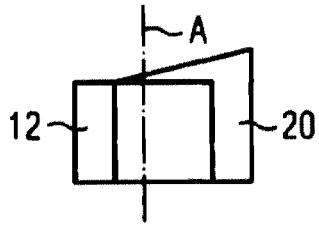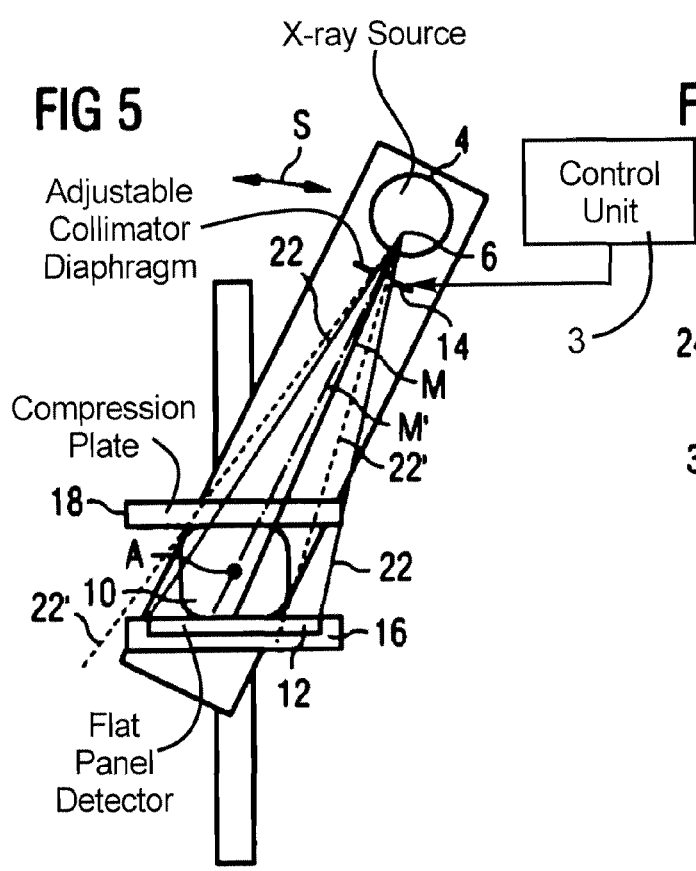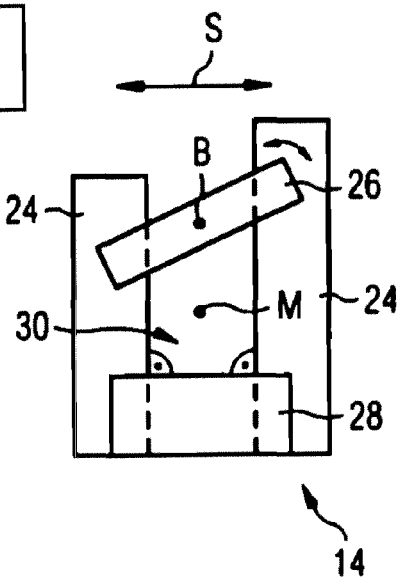

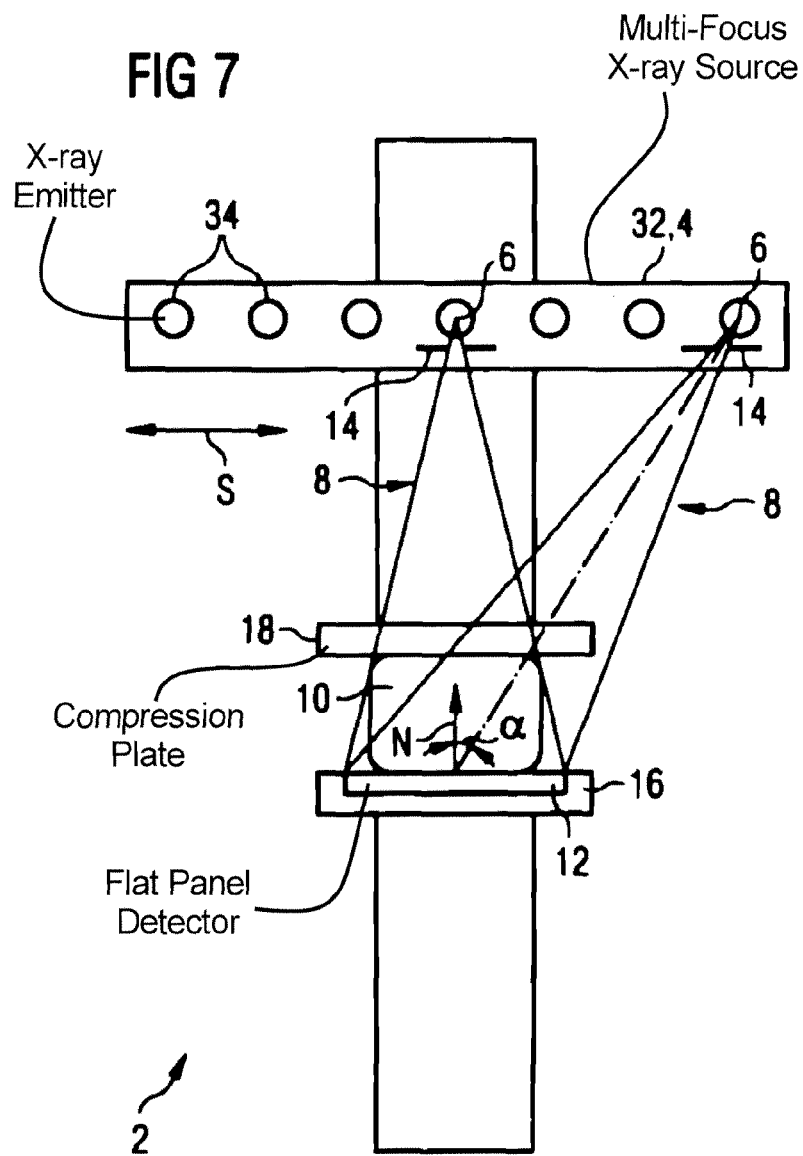

TOMOSYNTHESIS APPARATUS AND METHOD TO OPERATE A TOMOSYNTHESIS APPARATUS

BACKGROUND OF THE INVENTION

1. Field of the Invention

The present invention concerns a tomosynthesis apparatus as well as a method to operate a tomosynthesis apparatus.

2. Description of the Prior Art

Tomosynthesis is an x-ray-based 3D imaging method which is particularly suitable for use in mammography. Through continuous development it is sought to generate x-ray images with high significance in order to differentiate benign variations from malignant variations and to reduce the number of incorrect findings, i.e. the number of suspicious findings that are caused by non-malignant variations and the number of undiscovered malignant tumors.

An example of a tomosynthesis apparatus and operating method is described in DE 10 2006 024 413 A1.

In conventional mammography, a two-dimensional single image of the compressed breast is generated. In tomosynthesis of the breast, single images (projections) are respectively acquired from different directions, from which a tomosynthetic image data set is generated. The projections are used in a calculation to form tomosynthetic 3D x-ray image using image reconstruction methods. In this way structures can also be identified and examined that would occlude one another in a conventional mammogram that consists only of one x-ray image acquired from a single projection direction.

To acquire a tomosynthesis image data set, the examination subject (for example the breast) is irradiated from a number of different directions, to acquire the individual projections. The different directions from which the examination subject is exposed to acquire the individual projections are characterized by what are known as tomosynthesis angles. The different radiation directions or tomosynthesis angles are achieved by panning the x-ray source around the examination subject within a limited angle range, for example by ±20° starting from a center position. The x-ray source can thereby ensue in a plane perpendicular to the plane of the x-ray detector, as is typical in the tomosynthesis examination of the breast. The movement of the movement of the x-ray source and thus its x-ray focus, typically ensues essentially along a straight line or along a circular arc. In what is known as circular tomosynthesis, the x-ray source is moved in a plane oriented parallel to the detector plane. The x-ray focus thereby follows in a circular path, for example.

The x-ray detector (normally a flat panel detector) that receives (detects) the x-ray beam emanating from the x-ray source remains essentially stationary during the movement of the x-ray source, meaning that the x-ray detector actually remains stationary or is entrained only slightly in the direction opposite the movement of the tube.

The x-ray beam emanating from the x-ray source is limited by a collimator diaphragm so that the exposure of the flat panel detector is optimal. The exposure is considered as optimal when the entire detector area of the flat panel detector is utilized, i.e. is exposed. The radiation field at the location of the detector thus essentially corresponds to the detector area. The situation of the x-ray beam having a cross-section that, at the location of the flat panel detector, either exceeds the dimensions of the flat panel detector, or that has a portion that does not actually strike the flat panel detector, is referred to herein as an "overexposure."

As used herein, therefore, the term "overexposure" does not mean an unwanted darkening of the image, due to an excessively high radiation intensity or an excessively long exposure duration.

In conventional x-ray apparatuses, the collimator diaphragm is often placed or plugged by hand into a tray or a slot provided for the diaphragm. Normally a small metal lamella (thin plate) into which a fixed collimator diaphragm aperture is punched or milled, is used as the collimator diaphragm.

The collimation of the x-ray beam in tomosynthesis in which the x-ray source is moved relative to the detector has conventionally been achieved in a less than satisfactory manner. Both an insufficient exposure of the detector surface and overexposure of the detector have been observed from different tomosynthesis angles.

SUMMARY OF THE INVENTION

An object of the present invention is to provide a tomosynthesis apparatus and a method to operate a tomosynthesis apparatus wherein the exposure of the detector is improved.

The tomosynthesis apparatus according to the invention has an x-ray source that generates an x-ray beam emanating from a focus which is detected by a flat panel detector. To set a tomosynthesis angle, the position of the central axis of the x-ray beam of the x-ray source is variable. A collimator diaphragm has a diaphragm aperture that limits the expansion of the x-ray beam at the location of the flat panel detector. The collimator diaphragm is arranged in the beam path between the focus and the flat panel detector. The shape and size of the diaphragm aperture are dependent on the tomosynthesis angle, such that the expansion of the x-ray beam at the location of the flat panel detector essentially corresponds to the dimensions of the flat panel detector.

As used herein, a "tomosynthesis apparatus" refers to an x-ray apparatus to implement an x-ray-based tomosynthesis 3D imaging method. A distinction in comparison to computed tomography systems is that in a tomosynthesis apparatus, the examination subject is exposed only from a limited angle range. A tomosynthesis apparatus is particularly suitable to implement tomosynthetic examinations of the breast, for example within the scope of a mammogram. Such an apparatus, however, can also be used in a different field of medicine to acquire tomosynthesis image data sets. For example, a tomosynthesis apparatus can be suitable to implement a circular tomosynthesis in the field of dental technology.

As used herein, a "tomosynthesis angle" means either a simple angle or an angle composed of two components, depending on the acquisition geometry of the tomosynthesis apparatus. In the first case, the x-ray source of the tomosynthesis apparatus can be moved in a plane perpendicular to that of the detector. In this case, the tomosynthesis angle, is the angle between a surface normal of the flat panel detector and a central axis of the x-ray beam. In the second case, the tomosynthesis apparatus is used for circular tomosynthesis. The x-ray source of the tomosynthesis apparatus is thus essentially movable along a circular or elliptical path in a plane parallel to that of the detector. The tomosynthesis angle in this second case is composed of a polar component and an azimuthal component. The polar component is the angle between a surface normal of the flat panel detector and a central axis of the x-ray beam. The azimuthal component indicates the revolution position of the x-ray source. For example, the azimuthal component can be defined by an angle situated in the plane of the detector that is enclosed by two reference lines. The reference lines both proceed through a center point of the movement trajectory of the x-ray source that is projected in the detector plane; in the simplest case, this is thus the center point of the circle on which the x-ray source moves, projected in the detector plane. A first reference line is arbitrarily established in the detector plane; the second reference line proceeds through the incidence point of the central axis of the x-ray beam.

The aforementioned design of the tomosynthesis apparatus is based on the following insight:

It has been recognized that an optimal exposure of the flat panel detector can only be achieved when the shape and size of the collimator diaphragm is varied depending on the tomosynthesis angle. In particular, the following mathematical correlation was determined.

If $r_k=(x_k, y_k, z_k)$ designates a point in the plane of the collimator diaphragm, with the use of a projection matrix P, this is mapped to the point $r_d=(x_d, y_d, z_d)$ in the plane of the detector according to:

$$r_d = Pr_k.$$

The projection matrix P exactly describes the acquisition geometry. In order to now find the correct shape and size of the collimator diaphragm aperture with regard to every tomosynthesis angle, the inverse projection matrix $P^{-1}$ is used. Every point in the collimator diaphragm plane $r_k$ arises from a point $r_d$ in the detector plane according to $$r_k = p^{-1} \cdot r_d.$$

Since the shape of the flat panel detector is known and moreover is constant, the shape and size of the diaphragm aperture can easily be calculated. To avoid excessive calculation effort, the shape of the collimator diaphragm can be calculated using a few points in the detector plane, for example using the four corners (vertices) of the detector. An additional simplification results from the fact that the Z-coordinates of the points are predetermined both in the detector plane and in the collimator diaphragm plane by the position of the detector or, respectively, the position of the collimator diaphragm.

In the tomosynthesis apparatus according to the invention, an optimal exposure of the flat panel detector can be ensured at every tomosynthesis angle. The detector area is fully exploited and an overexposure of the detector that is undesirable for radiation protection reasons can be avoided. The tomosynthesis apparatus according to the invention ensures the largest possible image field with simultaneously the best possible radiation protection for personnel and patient.

According to a first embodiment, the x-ray source can be moved in a plane oriented essentially perpendicular to the flat panel detector. The tomosynthesis angle is the angle enclosed by a surface normal of the flat panel detector and a central axis of the x-ray beam. A tomosynthesis apparatus according to the preceding embodiment is in particular suitable to implement tomosynthesis examinations of the breast.

According to a further embodiment, the collimator diaphragm aperture is trapezoidal as viewed in the direction of the central axis of the x-ray beam, wherein two internal angles of the trapezoid advantageously amount to 90°. Tomosynthesis apparatuses to implement a tomosynthesis examination of the breast possess a geometry that is specifically suited for this type of examination. In these apparatuses the boundary ray of the x-ray beam used for examination, which boundary ray faces toward the chest wall, strikes the detector nearly perpendicularly in the perpendicular position of the system. The trapezoidal shape of the collimator diaphragm aperture arises from the following considerations:

If, within the scope of the acquisition of a tomosynthetic image data set, a projection ensues from a tomosynthesis angle≠0, a beam limited by a rectangular collimator diaphragm is distorted into a trapezoid in the plane of the detector. In order to now collimate the x-ray beam emanating from the x-ray source so that a rectangular detector is optimally exposed, the collimator diaphragm that is used must have the shape of a trapezoid.

The specific geometry of the trapezoid with two internal angles of 90° results from the already-typical design of a tomosynthesis for the implementation of tomosynthetic examinations of the breast as described above. These apparatuses use a geometry in which the x-rays strike the detector nearly perpendicularly on a side facing towards the patient (which is also designated as a chest wall side). Due to this geometry, given tomosynthesis angles≠0 the x-ray beam distorts in the plane only on the side facing away from the patient. A collimator diaphragm can consequently be used that corresponds to a trapezoid which possesses two internal angles=90°.

In the design of a tomosynthesis apparatus, in particular in a tomosynthesis apparatus for the implementation of tomosynthetic examination of the breast, the possibility exists to use a stationary, multi-focus x-ray source, or an x-ray source that can be panned can be used.

In an embodiment according to the first alternative, the x-ray source is a multi-focus x-ray source with a number of x-ray emitters that each generate an x-ray beam that is received by the flat panel detector. The x-ray emitters are arranged in parallel in a scan direction perpendicular to the surface normal of the flat panel detector. The emitters can be individually activated to vary the tomosynthesis angle. A collimator diaphragm that is located in the beam path between the focus of the x-ray emitter and the flat panel detector is associated with each of the x-ray emitters. The collimator diaphragm aperture respectively limits the expansion of the x-ray beam at the location of the flat panel detector such that the beam area (cross-section) essentially corresponds to the dimensions of the flat panel detector. In such a tomosynthesis apparatus, moving parts can advantageously be omitted. The shape and size of the collimator diaphragm aperture is respectively adapted to the position of the individual emitters, i.e. to the tomosynthesis angles from which the respective emitters expose the flat panel detector. In this way an exposure of the flat panel detector that is always optimal ensured for all emitters, i.e. for all tomosynthesis angles.

The second alternative is implemented according to a further embodiment. The x-ray source is moved together with the collimator diaphragm to vary the tomosynthesis angle. The shape and size of the collimator diaphragm aperture are controlled by a control unit depending on the tomosynthesis angle such that the expansion of the x-ray beam at the location of the flat panel detector always essentially corresponds to its dimensions. According to the preceding overview image, only one x-ray source with a collimator diaphragm whose shape and size are dynamically varied using the tomosynthesis angle is used to acquire different projections.

The same applies for a tomosynthesis apparatus which, according to a further embodiment, has an x-ray source in the form of a multi-focus x-ray source with a number of x-ray emitters. The individual x-ray emitters each generate an x-ray beam that is received by the flat panel detector. The x-ray emitters are arranged in parallel in a scan direction perpendicular to a surface normal of the flat panel detector, wherein the x-ray emitters can be individually activated to vary the tomosynthesis angle. The collimator diaphragm can be displaced in the scan direction. The shape and size of the collimator diaphragm aperture can be controlled by a control unit depending on the tomosynthesis angle such that the expansion of the x-ray beam at the location of the flat panel detector essentially corresponds to its dimensions.

The two preceding embodiments each use a single collimator diaphragm that follows the x-ray emission, in one case the x-ray source and in the other case the respective active emitter. The size and shape of the collimator diaphragm aperture are dynamically tracked so that an optimal exposure of the flat panel detector is always ensured.

In addition to being suitable for the implementation of tomosynthesis examinations of the breast, the tomosynthesis apparatuses according to the preceding embodiments are also suitable for the implementation of other tomosynthetic examinations. To acquire the individual projections, in a tomosynthesis apparatus which is suitable to implement a tomosynthetic examination of the breast the x-ray source is panned in one plane, i.e. moved along a circular arc or traveling linearly in this plane. The movement plane is oriented perpendicular to the flat panel detector. In a tomosynthesis apparatus, which is suitable for implementation of a circular tomosynthesis, the plane in which the x-ray source moves is oriented parallel to the plane of the flat panel detector. For example, the x-ray source can be moved along a circular track in this plane.

The invention also encompasses a method for the operation of a tomosynthesis apparatus having an x-ray source that generates an x-ray beam emanating from a focus. The x-ray beam is received by a flat panel detector, and the position of the central axis of the x-ray beam of the x-ray source can be varied to adjust a tomosynthesis angle. A collimator diaphragm whose collimator diaphragm aperture limits the expansion of the x-ray beam at the location of the flat panel detector is arranged in the beam path between the focus and the flat panel detector. The shape and size of the collimator diaphragm aperture are controlled in the operating method according to the invention such that the expansion of the x-ray emission at the location of the flat panel detector essentially corresponds to the detector dimensions.

The advantages of the method according to the invention for the operation of a tomosynthesis apparatus are comparable to the advantages cited in connection with the tomosynthesis apparatus according to the invention.

BRIEF DESCRIPTION OF THE DRAWINGS

FIG. 1 shows a mammography system in cross section.
FIGS. 2, 3 and 5 each show a mammography system in a frontal view.
FIGS. 4a, 4b and 4c show the shape of the exposed detector region.
FIG. 6 shows a diaphragm in plan view.
FIG. 7 shows a tomosynthesis apparatus with a multi-focus x-ray source in frontal view.

DESCRIPTION OF THE PREFERRED EMBODIMENTS

Figure 8:
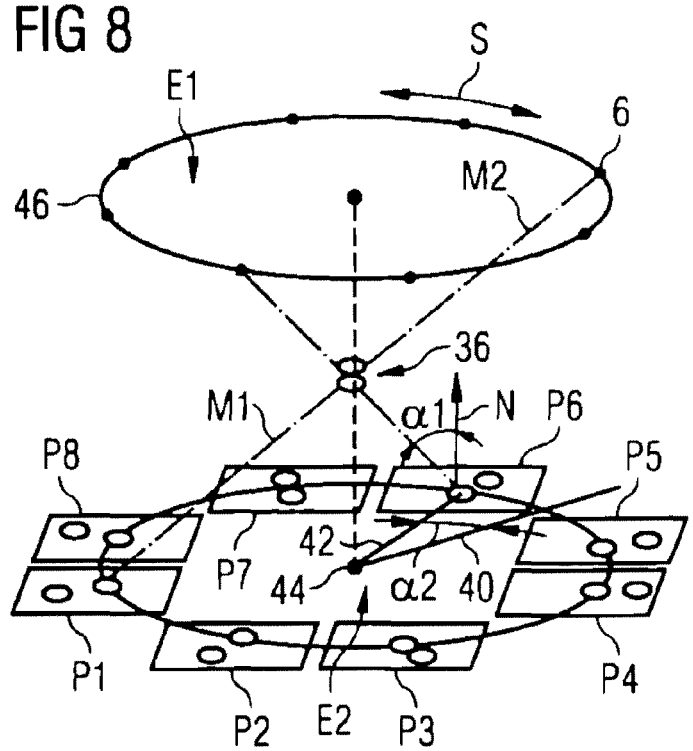
FIG. 8 is a schematic representation of the geometry of a circular tomosynthesis.

In the following reference is made to a tomosynthesis apparatus as well as its operating method using FIGS. 1 through 7, the operating method being suitable to implement tomosynthetic examinations of the breast. A tomosynthetic examination of the breast is abbreviated in the following as a tomosynthesis. Examples of circular tomosynthesis are likewise discussed using FIGS. 8 and 9.

FIG. 1 shows a tomosynthesis apparatus 2 with an x-ray source 4 that generates an x-ray beam 8 emanating from its focus 6, which x-ray beam 8 irradiates a breast 10 and is received by a flat panel detector 12. The x-ray beam 8 has a central axis M. The x-ray beam 8 is bounded to the sides by the collimator diaphragm 14 mounted in the beam path between the x-ray source 4 and the flat panel detector 12. The breast 10 is compressed between a bearing plate 16 into which the flat panel detector 12 is sunk and a compression plate 18. To acquire a tomosynthesis image data set, the breast 10 is held stationary between bearing plate 16 and compression plate 18 while the x-ray source 4 is panned around the axis A. The output of the flat panel detector 12, representing the projections (projection data sets) is supplied to a tomosynthesis image reconstruction computer 5, wherein a conventional tomosynthesis image reconstruction algorithm is executed in order to generate (reconstruct) a 3D image from the projection data sets supplied thereto.

FIG. 2 shows a tomosynthesis apparatus 2 at a tomosynthesis angle of 0°. FIG. 3 shows the tomosynthesis apparatus 2 at a tomosynthesis angle $\alpha \neq 0°$. The angle between a surface normal N of the flat panel detector 12 and the central axis M of the x-ray beam 8 is understood as a tomosynthesis angle $\alpha$. To acquire a tomosynthesis image data set, the x-ray source 4 is panned in a scan direction S. As a result of the panning motion, the region exposed by the x-ray beam 8 in the plane of the flat panel detector 12 is displaced. As is apparent in FIG. 3, at the tomosynthesis angle $\alpha$ that is shown there the right portion of the flat panel detector 12 is not exposed, in contrast to which it is overexposed at its left side. In addition to an underexposure and overexposure of the flat panel detector 12, a distortion of the projection of the x-ray beam in the plane of the flat panel detector 12 occurs as a result of the panning movement of the x-ray source 4.

FIGS. 4a, 4b and 4c show the projection 20 of the x-ray beam 8 in the plane of the flat panel detector 12 in relation to its area. FIG. 4a shows the situation shown in FIG. 3, in which the flat panel detector 12 is not sufficiently exposed on its right side and is overexposed on its left side. FIG. 4b shows the situation shown in FIG. 2 given a tomosynthesis angle $\alpha=0°$. The flat panel detector 12 and the projection 20 of the x-ray beam 8 are congruent. FIG. 4c shows the case in which the x-ray source 4 is panned to the left (contrary to the scan direction S shown in FIG. 3) and the flat panel detector 12 is corresponding underexposed on its left side and overexposed on its right side.

To avoid this phenomenon, in accordance with the invention the collimator diaphragm 11 is dynamically adapted (i.e., modified during the acquisition of the projections) in shape and size to the changing tomosynthesis angle $\alpha$. The effect of this adaptation is shown in FIG. 5. The x-ray beam 8 emanating from the x-ray source 4 is shown with dashed line and dashed reference character according to the situation shown in FIG. 3, in which the collimator diaphragm 14 was not adapted to the tomosynthesis angle $\alpha$. The situation after adaptation of the collimator diaphragm 14 to the tomosynthesis angle $\alpha$ is shown with solid line and solid reference character. The x-ray beam 8 emanating from the x-ray source 4 is limited by the collimator diaphragm 14 according to its boundary rays 22. The adaptation of the collimator diaphragm 14 now ensures that the flat panel detector 12 is also optimally exposed at tomosynthesis angles $\alpha \neq 0$. The dynamic variation of the collimator diaphragm 14 depending on the tomosynthesis angle $\alpha$ is possible by the collimator diaphragm 14 being composed of individual plates (as shown in FIG. 6). Given the movement of the x-ray source 4 in the scan direction S, shape and size of the diaphragm aperture 30 is controlled by a control unit 3 depending on the tomosynthesis angle α (see FIG. 3).

The collimator diaphragm 14 has two side lamellae 14, a rotating lamella 26 and a fixed lamella 28. The side lamellae 24 are essentially oriented perpendicular to the scan direction S. The distance of the side lamellae 24 from the central axis M of the x-ray beam 8 passing through the diaphragm aperture 30 can be varied in the scan direction S. An adaptation of the position of the side lamellae 24 prevents the flat panel detector 12 from being underexposed or overexposed in its lateral regions. The distance of the side lamellae 24 from the central axis M of the x-ray beam 8 can be varied to different degrees. This asymmetrical displacement of the side lamellae 24 is dependent on the tomosynthesis angle α as well as possibly on the scan direction S. The diaphragm aperture 3 is bounded by the fixed lamella 28 on that side of the diaphragm 14 that is facing towards a patient. The inner edges of the side lamellae 24 and the inner edge of the fixed lamella 28 that limits the diaphragm aperture 30 in this region advantageously exhibit an angle of 90° relative to one another. Since the projection of the x-ray beam 8 in the plane of the flat panel detector 12 does not vary on the side facing towards the patient (as this is shown in FIG. 4a through c), the diaphragm aperture 30 in this region can be limited by the fixed lamella 28.

On the opposite side, the diaphragm aperture 30 is bounded by the rotating lamella 26. This is borne in the plane of the diaphragm 14 such that it can be panned around an axis B. The rotating lamella 26 is now panned depending on the tomosynthesis angle α such that this forms a rectangular diaphragm aperture 30 at a tomosynthesis angle of α=0°, in contrast to which the rotating lamella 26 is panned given tomosynthesis angles α≠0° such that the diaphragm aperture 30 assumes the shape of a trapezoid.

The position of the diaphragm 14 that is shown in FIG. 6 corresponds to the position of the tomosynthesis apparatus 2 shown in FIG. 5. In order to avoid the x-ray beam 8 overexposing the flat panel detector 12 in the left region (as shown in FIG. 4a), the left side lamella 24 approaches the central axis M of the x-ray beam 8 passing through the diaphragm aperture 30 while the right side lamella 24 is removed from the central axis M. To avoid an overexposure of the flat panel detector 12 on the side facing away from the patient (in particular in the upper left region, see FIG. 4a), the rotating lamella 26 is panned such that this more strongly dims this upper left region.

FIG. 7 shows a tomosynthesis apparatus 2 with a multi-focus x-ray source 32 as an x-ray source 4. This has a number of x-ray emitters 34 that are each operable to generate an x-ray beam 8 that is received by the flat panel detector 12. A collimator diaphragm 14 whose diaphragm aperture is selected so that the x-ray beam 8 emitted by the x-ray emitter 34 is limited to the size of the flat panel detector 12 is associated with each of the x-ray emitters 34. The x-ray emitters 34 are essentially arranged in parallel perpendicular to the surface normal N of the flat panel detector 12 in the scan direction S. To vary the tomosynthesis angle α, the x-ray emitters 34 of the multi-focus x-ray source 32 are excited in the order of the scan direction S to emit an x-ray beam 8.

Alternatively, the tomosynthesis apparatus 2 shown in FIG. 7 can be equipped with a diaphragm 14 that can be displaced in the scan direction S, which diaphragm 14 is (as already mentioned in connection with FIGS. 5 and 6) varied in its shape and size depending on the tomosynthesis angle α. In such a case, the collimator diaphragm 14 is respectively brought into the beam path of that x-ray emitter 34 that is excited to emit an x-ray beam 8.

FIG. 8 schematically shows the geometry of a circular tomosynthesis. In this the focus 6 of an x-ray source 4 moves in a focus plane E1 that is oriented parallel to the detector plane E2 in which the flat panel detector 12 extends. An examination subject 36 is exposed from different tomosynthesis angles. The tomosynthesis angle thereby consists of two components, a polar angle α1 and an azimuthal angle α2. The polar angle α1 is the angle between a surface normal N of the flat panel detector and a central axis M1, M2 of the x-ray beam. The azimuthal angle α2 indicates the revolution direction of the x-ray source 4. In FIG. 8, the azimuthal angle α2 is the angle situated in the detector plane E2 that is enclosed by two reference lines 40, 42. The reference lines 40, 42 both proceed through a center point 44 of the movement trajectory 46 of the x-ray focus 6 that is projected in the detector plane E2. In FIG. 8, the focus 6 of the x-ray tube moves along a circular track. The first reference line 40 is arbitrarily established in the detector plane E2; the second reference line 42 proceeds through the incidence point of the central axis M1, M2 of the x-ray beam.

In FIG. 8 the central axes M1 and M2 of two of the x-ray beams 8 exposing the examination subject 36 are shown as examples. The structures of the examination subject 36 are shown depending on the tomosynthesis angles α1, α2 at different positions of the respective acquired projections P1 through P8.

For the implementation of a circular tomosynthesis, it is necessary for the collimator diaphragm 14 to be continuously adapted in terms of its shape and size. The adaptation of the collimator diaphragm 14 ensues depending on the tomosynthesis angles α1, α2, i.e. on the position of the focus 6 of the x-ray source 4 that moves along a circular path in the focus plane E1.

Figure 9:
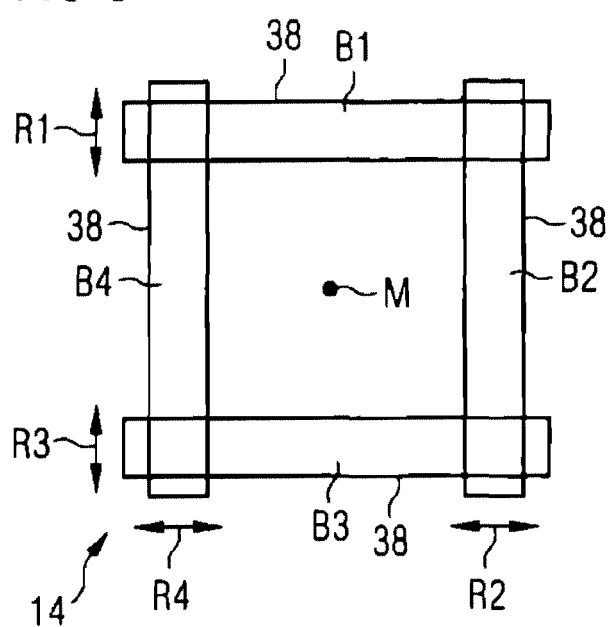
FIG. 9 shows a diaphragm suitable for the circular tomosynthesis, in plan view.

The adaptation of the collimator diaphragm 14 as is shown in the example in FIG. 9 ensues both by rotation and by displacement of the individual lamellae 38 of the collimator diaphragm 14. Depending on the tomosynthesis angle α1, α2, the individual lamellae 38 are individually rotated around their respective rotation axes B1 through B4 and are individually displaced in a displacement direction R1 through R4 relative to the central axis M of the x-ray beam passing through the collimator diaphragm 14. The collimator diaphragm 14 shown in FIG. 9 is suitable for use in tomosynthesis apparatuses 2, for example in the field of dental technology.

Although modifications and changes may be suggested by those skilled in the art, it is the intention of the inventors to embody within the patent warranted hereon all changes and modifications as reasonably and properly come within the scope of their contribution to the art.

We claim as our invention:

1. A tomosynthesis apparatus comprising:
    an x-ray source that emits an x-ray beam from a focus, said x-ray beam having a central beam axis;
    a flat panel detector that is irradiated by said x-ray beam and that generates a detector output signal dependent on radiation incident on said flat panel detector, said flat panel detector having an active detector area having flat panel detector dimensions, said x-ray source and said flat panel detector are adapted to receive a patient therebetween;
    said focus being movable in a scan direction relative to said flat panel detector to set a tomosynthesis angle at which said central beam axis is incident on said flat panel detector, said focus being movable through a plurality of different tomosynthesis angles to irradiate said flat panel detector respectively from different directions for which respective projection data sets are generated at the output of said flat panel detector;
a collimator diaphragm located in a path of said x-ray beam between said focus and said flat panel detector, said collimator diaphragm having a diaphragm aperture that limits a size and shape of said x-ray beam, said diaphragm aperture being adjustable in size and shape;
said collimator diaphragm comprising two side lamellae, respectively located at and defining opposite sides of said diaphragm aperture, said two side lamellae each being oriented substantially perpendicularly to said scan direction and having a spacing from said central beam axis that is adjustable by said control unit substantially parallel to said scan direction dependent on said tomosynthesis angle;
said collimator diaphragm comprising a fixed lamella that is located at and defines a side of said diaphragm aperture facing toward the patient, said fixed lamella having a spacing from said central beam axis that is constant as said tomosynthesis angle changes, said side lamellae each being disposed at an angle of 90° relative to said fixed lamella;
said collimator diaphragm comprising a rotating lamella mounted in said collimator diaphragm to rotate in a plane of said diaphragm aperture, said rotating lamella being rotated by said control unit to limit said diaphragm aperture at a side thereof facing away from the patient;
a control unit connected to said collimator diaphragm that dynamically adjusts the size and shape of said diaphragm aperture dependent on the changing tomosynthesis angle to always cause an area of said x-ray beam that irradiates said flat panel detector to substantially correspond to said flat panel detector dimensions; and
a tomosynthesis image reconstruction computer supplied with said projection data sets from said flat panel detector, configured to execute an image reconstruction algorithm to reconstruct a three-dimensional tomosynthesis image from said projection data sets, said tomosynthesis image reconstruction computer making said three-dimensional tomosynthesis image available at an output thereof.

2. A tomosynthesis apparatus as claimed in claim 1 wherein said x-ray source is mounted for movement in a plane proceeding substantially perpendicularly to said flat panel detector, and wherein said tomosynthesis angle is an angle encompassed by a surface normal of said flat panel detector and the central beam axis.

3. A tomosynthesis apparatus as claimed in claim 2 wherein said diaphragm aperture of said collimator diaphragm is trapezoidal as seen in a direction of said central beam axis.

4. A tomosynthesis apparatus as claimed in claim 3 wherein said trapezoid comprises at least two internal angles of 90°.

5. A tomosynthesis apparatus as claimed in claim 1 wherein said collimator diaphragm comprises at least one lamella that is mounted in said collimator diaphragm to be movable by said control unit through a plane of said diaphragm aperture.

6. A tomosynthesis apparatus as claimed in claim 5 wherein said collimator diaphragm comprises four lamellae that are mounted in said collimator diaphragm and are movable by said control unit in the plane of the diaphragm aperture.

7. A tomosynthesis apparatus comprising:
a multi-focus x-ray source comprising a plurality of foci, each of said foci serving as an x-ray emitter from which an x-ray beam is generated, each x-ray beam having a central beam axis;
a flat panel detector that is irradiated by said x-ray beams and that generates a detector output signal dependent on radiation incident on said flat panel detector, said flat panel detector having an active detector area having flat panel detector dimensions;
said foci being movable in a scan direction relative to said flat panel detector to set a tomosynthesis angle at which each central beam axis is incident on said flat panel detector, said foci being movable through a plurality of different tomosynthesis angles to irradiate said flat panel detector respectively from different directions for which respective projection data sets are generated at the output of said flat panel detector;
said x-ray emitters being arranged in parallel along said scan direction perpendicular to a surface normal of said flat panel detector;
said x-ray emitters being individually activated to vary said tomosynthesis angle;
a plurality of individual collimator diaphragms respectively associated with said x-ray emitters, each individual collimator diaphragm being located between the associated x-ray emitter and the flat panel detector, each collimator diaphragm having a diaphragm aperture that limits a size and shape of the x-ray beam emitted by the x-ray emitter associated therewith;
a control unit connected to the individual diaphragms the respectively controls the individual collimator diaphragms to cause each x-ray beam emitted by each x-ray emitter to always have a cross section at said flat panel detector that substantially corresponds to said flat panel detector dimensions; and
a tomosynthesis image reconstruction computer supplied with said projection data sets from said flat panel detector, configured to execute an image reconstruction algorithm to reconstruct a three-dimensional tomosynthesis image from said projection data sets, said tomosynthesis image reconstruction computer making said three-dimensional tomosynthesis image available at an output thereof.

8. A tomosynthesis apparatus comprising:
a multi-focus x-ray source comprising a plurality of foci, each of said foci serving as an x-ray emitter from which an x-ray beam is generated, each x-ray beam having a central beam axis;
a flat panel detector that is irradiated by said x-ray beam and that generates a detector output signal dependent on radiation incident on said flat panel detector, said flat panel detector having an active detector area having flat panel detector dimensions;
said foci being movable in a scan direction relative to said flat panel detector to set a tomosynthesis angle at which each central beam axis is incident on said flat panel detector, said foci being movable through a plurality of different tomosynthesis angles to irradiate said flat panel detector respectively from different directions for which respective projection data sets are generated at the output of said flat panel detector;
said x-ray emitters being arranged in parallel along said scan direction perpendicular to a surface normal of said flat panel detector;
said x-ray emitters being individually activated to vary said tomosynthesis angle;

said collimator diaphragm being movable in said scan direction perpendicular to a surface normal of said flat detector through a plurality of positions respectively associated with said x-ray emitters, at each position said collimator diaphragm being located between the associated x-ray emitter and the flat panel detector;

a control unit that controls movement of the collimator diaphragm to cause each x-ray beam emitted by each x-ray emitter to always have a cross section at said flat panel detector that substantially corresponds to said flat panel detector dimensions; and a tomosynthesis image reconstruction computer supplied with said projection data sets from said flat panel detector, configured to execute an image reconstruction algorithm to reconstruct a three-dimensional tomosynthesis image from said projection data sets, said tomosynthesis image reconstruction computer making said three-dimensional tomosynthesis image available at an output thereof.

9. A tomosynthesis method comprising the steps of:

emitting an x-ray beam from a focus, said x-ray beam having a central beam axis;

irradiating a flat panel detector with said x-ray beam to generate a detector output signal dependent on radiation incident on said flat panel detector, said flat panel detector having an active detector area having flat panel detector dimensions;

placing a patient between said x-ray source and said flat panel detector;

moving said focus being movable in a scan direction relative to said flat panel detector to set a tomosynthesis angle at which said central beam axis is incident on said flat panel detector, by moving said focus through a plurality of different tomosynthesis angles to irradiate said flat panel detector respectively from different directions for which respective projection data sets are generated at the output of said flat panel detector;

passing said x-ray beam through a diaphragm aperture in a collimator diaphragm located in a path of said x-ray beam between said focus and said flat panel detector, and with said a diaphragm aperture, limiting a size and shape of said x-ray beam, said diaphragm aperture being adjustable in size and shape;

forming said collimator diaphragm with two side lamellae, respectively located at and defining opposite sides of said diaphragm aperture, said two side lamellae each being oriented substantially perpendicularly to said scan direction and adjusting a spacing from said central beam axis of each of said side lamellae with said control unit substantially parallel to said scan direction dependent on said tomosynthesis angle, and with a fixed lamella that is located at and defines a side of said diaphragm aperture facing toward the patient, and maintaining a spacing of said fixed lamella from said central beam axis constant as said tomosynthesis angle changes, said side lamellae each being at an angle of 90° relative to said fixed lamella;

forming said collimator diaphragm further with a rotatinq lamella mounted in said collimator diaphragm to rotate in a plane of said diaphragm aperture, and rotating said rotating lamella with said control unit to limit said diaphragm aperture at a side thereof facing away from the patient;

operating said collimator diaphragm with a control unit to dynamically adjust the size and shape of said diaphragm aperture dependent on the changing tomosynthesis angle to always cause an area of said x-ray beam that irradiates said flat panel detector to substantially correspond to said flat panel detector dimensions; and in a tomosynthesis image reconstruction computer supplied with said projection data sets from said flat panel detector, executing an image reconstruction algorithm to reconstruct a three-dimensional tomosynthesis image from said projection data sets, and making said three-dimensional tomosynthesis image available at an output of said tomosynthesis image reconstruction computer.

10. A tomosynthesis method as claimed in claim 9 comprising moving said x-ray focus in a plane proceeding substantially perpendicularly to said flat panel detector, and wherein said tomosynthesis angle is an angle encompassed by a surface normal of said flat panel detector and the central beam axis.

11. A tomosynthesis method as claimed in claim 10 comprising configuring said diaphragm aperture of said collimator diaphragm as trapezoidal as seen in a direction of said central beam axis.

12. A tomosynthesis method as claimed in claim 11 comprising configuring said diaphragm aperture as a trapezoid comprising at least two internal angles of 90°.

13. A tomosynthesis method as claimed in claim 9 comprising forming said collimator diaphragm with at least one lamella that is mounted in said collimator diaphragm to be movable by said control unit through a plane of said diaphragm aperture.

14. A tomosynthesis method as claimed in claim 13 comprising forming said collimator diaphragm with four lamellae that are mounted in said collimator diaphragm and are movable by said control unit in the plane of the diaphragm aperture.

15. A tomosynthesis method comprising:

emitting multiple x-ray beams from a multi-focus x-ray source comprising a plurality of foci, each of said foci serving as an x-ray emitter from which an x-ray beam is generated, each x-ray beam having a central beam axis;

irradiating a flat panel detector with said x-ray beams to generate a detector output signal dependent on radiation incident on said flat panel detector, said flat panel detector having an active detector area having flat panel detector dimensions;

moving said foci being in a scan direction relative to said flat panel detector to set a tomosynthesis angle at which each central beam axis is incident on said flat panel detector, by moving said foci through a plurality of different tomosynthesis angles to irradiate said flat panel detector respectively from different directions for which respective projection data sets are generated at the output of said flat panel detector;

arranging said x-ray emitters in parallel along said scan direction perpendicular to a surface normal of said flat panel detector;

individually activating said x-ray emitters to vary said tomosynthesis angle;

collimating said x-ray beams individually with a plurality of individual collimator diaphragms respectively associated with said x-ray emitters, each individual collimator diaphragm being located between the associated x-ray emitter and the flat panel detector, each collimator diaphragm having a diaphragm aperture located in a path of the x-ray beam of the associated emitter between said focus and said flat panel detector, said diaphragm aperture being adjustable in size and shape and with each diaphragm aperture, limiting a size and shape of the x-ray beam of the associated x-ray emitter;

operating each collimator diaphragm with a control unit to dynamically adjust the size and shape of said diaphragm aperture dependent on the changing tomosynthesis angle to always cause each x-ray beam emitted by each x-ray emitter to always have a cross-section that substantially corresponds to said flat panel detector dimensions; and in a tomosynthesis image reconstruction computer supplied with said projection data sets from said flat panel detector, executing an image reconstruction algorithm to reconstruct a three-dimensional tomosynthesis image from said projection data sets, and making said three-dimensional tomosynthesis image available at an output of said tomosynthesis image reconstruction computer.

16. A tomosynthesis method comprising:

emitting multiple x-ray beams from a multi-focus x-ray source comprising a plurality of foci, each of said foci serving as an x-ray emitter from which an x-ray beam is generated that irradiates said flat panel detector, each x-ray beam having a central beam axis;

irradiating a flat panel detector with said x-ray beams to generate a detector output signal dependent on radiation incident on said flat panel detector, said flat panel detector having an active detector area having flat panel detector dimensions;

moving said foci in a scan direction relative to said flat panel detector to set a tomosynthesis angle at which each central beam axis is incident on said flat panel detector, by moving said foci through a plurality of different tomosynthesis angles to irradiate said flat panel detector respectively from different directions for which respective projection data sets are generated at the output of said flat panel detector;

arranging said x-ray emitters in parallel along said scan direction perpendicular to a surface normal of said flat panel detector;

individually activating said x-ray emitters to vary said tomosynthesis angle;

passing said x-ray beam through a diaphragm aperture in a collimator diaphragm located in a path of each x-ray beam between the focus thereof and said flat panel detector, said diaphragm aperture being adjustable in size and shape and with said diaphragm aperture, limiting a size and shape of each x-ray beam;

moving said collimator diaphragm in said scan direction perpendicular to a surface normal of said flat detector through a plurality of positions respectively associated with said x-ray emitters, at each position said collimator diaphragm being located between the associated x-ray emitter and the flat panel detector;

operating said collimator diaphragm with a control unit to dynamically adjust the size and shape of said diaphragm aperture dependent on the changing tomosynthesis angle to always cause each x-ray beam emitted by each x-ray emitter to always have a cross-section that substantially corresponds to said flat panel detector dimensions; and in a tomosynthesis image reconstruction computer supplied with said projection data sets from said flat panel detector, executing an image reconstruction algorithm to reconstruct a three-dimensional tomosynthesis image from said projection data sets, and making said three-dimensional tomosynthesis image available at an output of said tomosynthesis image reconstruction computer.

* * * * *